United States Patent [19]

Fortunak et al.

[11] Patent Number: 5,155,225
[45] Date of Patent: Oct. 13, 1992

[54] METHOD FOR MAKING CERTAIN PYRANO[3',4':6,7]INDOLIZINO-[1,2-B]QUINOLINONES

[75] Inventors: Joseph M. Fortunak, Exton; Mark Mellinger, Telford; Jeffery L. Wood, Blue Bell, all of Pa.

[73] Assignee: SmithKline Beecham Corporation, Philadelphia, Pa.

[21] Appl. No.: 589,848

[22] Filed: Sep. 28, 1990

[51] Int. Cl.$^5$ .............................. C07D 471/04
[52] U.S. Cl. ..................................... 546/70
[58] Field of Search ..................... 546/70, 48

[56] References Cited

PUBLICATIONS

Kingsbury, "Chemical Rearrangement of Comptothecin . . . ", Tetrahedron Lett. 29(52), 6847–50, 1988.
Hertzberg, "Modification of the hydroxylactone ring . . . ", J. Med. Chem. 32(3) 715–20, 1989.

*Primary Examiner*—Marianne M. Cintins
*Assistant Examiner*—Catherine S. Kilby Scalzo
*Attorney, Agent, or Firm*—Yuriy P. Stercho; Stuart R. Suter; Edward T. Lentz

[57] ABSTRACT

A method for making 8-methyl-7-(1-oxopropyl)indolizino[1,2-b]quinolin-9(11H)-ones from 4-ethyl-4-hydroxy-1H-pyrano[3',4':6,7]indolizino[1,2-b]quinolin-3,14(4H,12H)-diones, said method being graphically illustrated as follows:

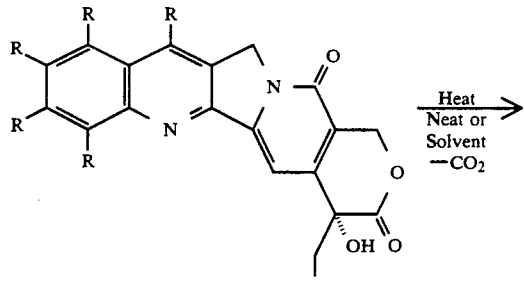

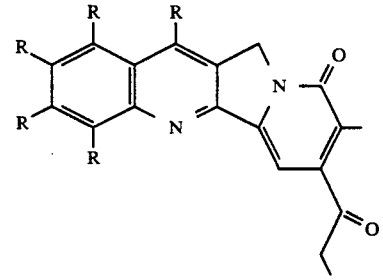

5 Claims, No Drawings

METHOD FOR MAKING CERTAIN PYRANO[3',4':6,7]INDOLIZINO-[1,2-B]QUINOLINONES

SCOPE OF THE INVENTION

This invention relates to a method for making certain 8-methyl-7-(1-oxopropyl)indolizino[1,2-b]quinolin-9(11H)-ones from 4-ethyl-4-hydroxy-1H-pyrano[3',4':6,7]indolizino[1,2-b]quinolin3,14(4H,12H)-diones.

BACKGROUND

Certain 1H-pyrano[3',4',6,7]indolizino[1,2-b]quinolinones are known to have cytotoxic and antiviral activity. Camptothecin {4-ethyl-4-hydroxy-1H-pyrano[3',4':6,7]indolizino[1,2-b]quinolin3,14(4H),12H)-dione} is an example of one such compound. It is a water-insoluble, cytotoxic alkaloid produced by *Camptotheca accuminata* plants indigenous to China and *Nothapodytes foetida* plants indigenous to India. Camptothecin and a few close congeners thereof are the only class of compounds known to inhibit eukaryotic topoisomerase I. Camptothecin (and its known congeners) have no effect on topoisomerase II and none of the known topoisomerase II inhibitors has any significant effect on topoisomerase I.

Certain modifications to the camptothecin molecule have produced compounds which have antiviral activity, but are not cytotoxic or have little cytotoxicity. One of these modifications is that of opening the E ring in camptothecin in a way which gives a 8-methyl-7-(1-oxopropyl)indolizino[1,2-b]quinolin-9(11H)-one. These compounds and analogs have useful antiviral activity. Such compounds are disclosed in co-pending application Ser. No. 07/589,643, of Patrick L. Burk et al., filed on even date herewith.

This invention provides a method for making certain 8-methyl-7-(1-oxopropyl)indolizino[1,2-b]quinolin-9(11H)-ones. These ketones can be used for preparing other antiviral agents where the indolizino or quinolino portions of these compounds are substituted.

SUMMARY OF THE INVENTION

This invention relates to a method for making a 8-methyl-7-(1-oxopropyl)indolizino[1,2-b]quinolin-9(11H)-one of formula I,

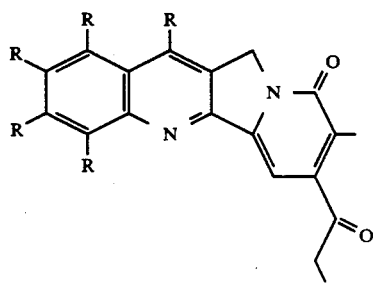

(I)

which method comprises heating to about 100° C. or higher a 4-ethyl-4-hydroxy-1H-pyrano[3',4':6,7]indolizino[1,2-b]quinolin-3,14(4H,12H)-dione of the formula II

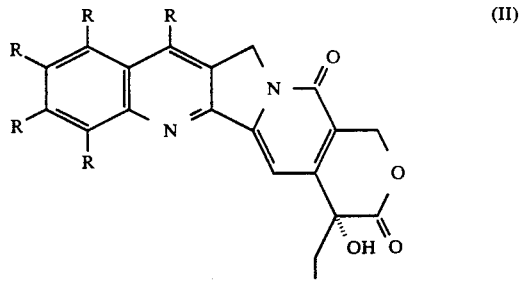

(II)

neat or in a solvent.

SPECIFIC EMBODIMENTS

The reaction is useful for making compounds of formula I which is unsubstituted, or substituted with one or more substituents, represented by the R designation in formula I. The only limitation is that the R substituent, if it is other than hydrogen, is not affected during the heating process used to make formula I.

Graphically it can be illustrated as follows.

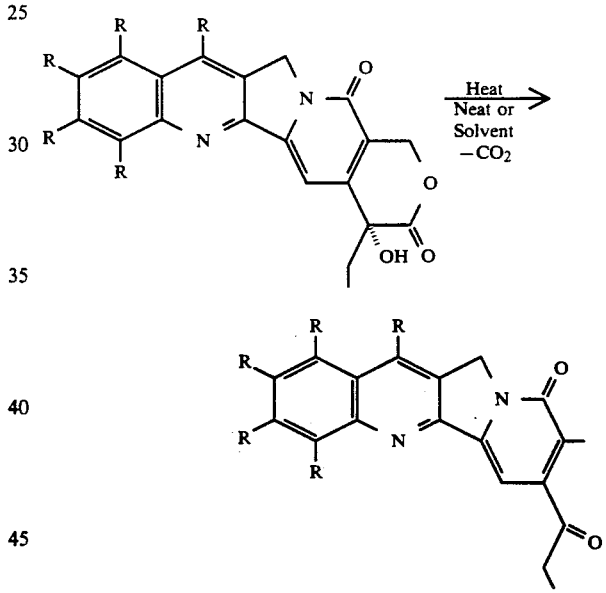

This efficient process can be carried by heating the compound either neat or in an appropriate solvent. Useful temperatures are those at which the reaction proceeds at a reasonable rate and which do not pyrolytically degrade another site on the ring of formula II, or degrades an R substituent. Too low a temperature, while it may cause loss of $CO_2$, will proceed so slowly as to be of no practical use. It is preferred that a temperature in excess of 100° C. be used for efficient operation of this reaction. The only limitation on temperature is that operation of this reaction. The only limitation on temperature is that it not be so high as to cause unwanted degradation of the molecule. The most preferred temperature range is between about 150°-200° C.

Solvents may be used in practicing this invention. There is no limitation on what solvents may be used other than it must have a boiling point at or higher than the temperature at which the reaction is to be carried out. Secondly, the solvent itself must be inert with respect to the reaction. In other words, the solvent must not interfere with the reaction in the sense of reacting with the molecule or in some means having an untoward or deleterious affect on the reaction or reactant.

Two preferred solvents are N,N-dimethylformamide and triethylene glycol dimethyl ether (triglyme).

EXAMPLES

Example 1

8-methyl-7-(1-oxopropyl)indolizino[1,2-b]quinolin-9(11H)-one

A sample of 4.6 g of 4-ethyl-4-hydroxy-1H-pyrano[3',4':6,7]-indolizino[1,2-b]quinolin-3,14(4H,12H)-dione [(20 S) camptothecin] was stirred with 46 ml of N,N-dimethylformamide. The suspension was heated at reflux, and the disappearance of starting material was monitored by HPLC (C18 reverse phase column, 20–25% acetonitrile:water mobile phase, perchlorate buffer at pH approximately 3.0). The reaction was monitored by UV detection at a wavelength of 228 nm. The only responses detected under these conditions were a peak for N,N-dimethylformamide near the solvent front, a peak for the starting material and a peak for the desired product with a retention time of approximately 3.2 relative to the starting material. The reaction was heated until consumption of the starting material was complete (approximately 8 days). After cooling to ambient temperature the solid product was collected by filtration, and washed with methanol. After drying under vacuum to a constant weight 3.48 g (87%) of product, m.p. 233°–234° C. was obtained.

Example 2

10-hydroxy-8-methyl-7-(1-oxopropyl)indolizino[1,2-b]-quinolin-9(11H)-one

A stirred suspension of 4.0 g of 10-hydroxycamptothecin in 50 ml of triethylene glycol dimethyl ether (triglyme) was heated at approximately 200 degrees C. The reaction was monitored by HPLC using the conditions of the preceding example. A relative retention time of approximately 3.05 was obtained for the product versus the starting material. The reaction suspension gradually formed a golden yellow solution over about 2.5 hours. After 6.5 hours the starting material was completely consumed. The reaction was cooled to ambient temperature with stirring over 17 hours. The suspension was diluted with 100 ml of diethyl ether, and after stirring for an additional 2 hours, the solid product was collected by filtration and dried to a constant weight. The recovered product, m.p.>315° C., weighed 3.35 g (95%).

What is claimed is:

1. A method for making a 8-methyl-7-(1-oxopropyl)indolizino[1,2-b]quinolin-9(11H)-one of formula I

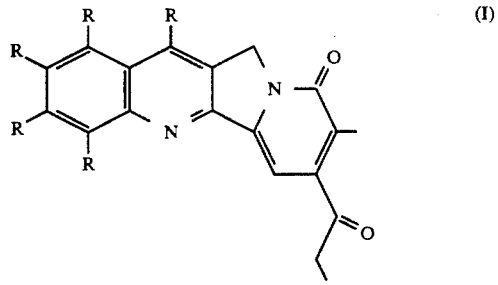

where R represents hydrogen or another substituent, which method consists essentially of heating to about 150°–200° C. a 4-ethyl-4-hydroxy-1H-pyrano[3',4':6,7]indolizino[1,2-b]quinolin-3,14(4H,12H)-dione of the formula II

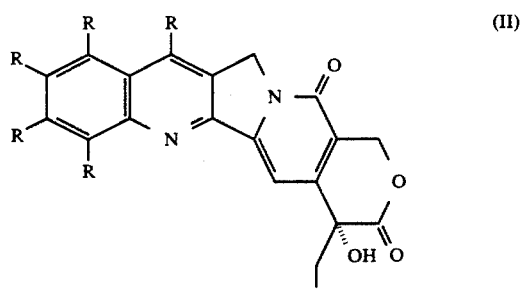

neat or in a solvent.

2. The process of claim 1 where the product is 8-methyl-7-(1-oxopropyl)indolizino[1,2-b]quinolin-9(11H)-one.

3. The process of claim 2 which is carried out in N,N-dimethylformamide at about reflux.

4. The process of claim 1 where one or more of the R groups is other than hydrogen.

5. The process of claim 4 which is carried out in triglyme at a temperature of about 200° C.

* * * * *